United States Patent [19]

Gordon

[11] Patent Number: 4,522,805

[45] Date of Patent: Jun. 11, 1985

[54] TOOTH AND GUM DENTIFRICE

[76] Inventor: Norman Gordon, 114 Sussex Rd., New Rochelle, N.Y. 10804

[21] Appl. No.: 502,142

[22] Filed: Jun. 8, 1983

[51] Int. Cl.³ .................. A61K 7/16; A61K 7/20; A61K 7/18

[52] U.S. Cl. .................... 424/52; 424/49; 424/53

[58] Field of Search .................. 424/49–58

[56] References Cited

U.S. PATENT DOCUMENTS

| | | | |
|---|---|---|---|
| 3,885,028 | 5/1975 | Cella et al. | 424/52 |
| 3,937,804 | 2/1976 | Delaney et al. | 424/52 |
| 4,302,441 | 11/1981 | Muhlemann et al. | 424/53 |

FOREIGN PATENT DOCUMENTS 1209319 10/1970 United Kingdom ................ 424/53

OTHER PUBLICATIONS

Zinner et al, Dental Abstr. 16: 615, Oct. 1971, of Pharmacol. Ther. Dent. 1: 7–15 Oct. 1970, Effect of Oxygen Gel on Plaque and Oral Debris.

Manhold et al, J. Periodontol., 45(5): 312–313 (1974) "Gingival Tissue Oxygenation: The Effect of Daily Application of Four Commercial Applications".

*Primary Examiner*—Shep K. Rose
*Attorney, Agent, or Firm*—Arthur T. Fattibene

[57] ABSTRACT

A tooth and gum dentifrice formed as a stable paste formulated of sodium bicarbonate, calcium carbonate, urea peroxide, sodium flouride and a paste carrier which includes a synthetic detergent, humectant sorbitol and a thickening agent or binder, and which functions to effect a synergistic chemical and mechanical action to remove dental plaque from teeth and reduce bacteria so as to aid in the control and reduction of incipient periodontal disease and minimize dental caries.

4 Claims, No Drawings

TOOTH AND GUM DENTIFRICE

PRIOR ART

Various compositions and compounds are known for use as a dentifrice. Some of the known dentifrice type compounds or compositions are disclosed in U.S. Pat. Nos. 2,218,172; 3,227,617; 4,160,022; 4,181,621; 4,267,167; 4,302,441. However, as described therein, each is directed to a stated formulation and for a specific purpose. Generally, the known dentifrice compositions are formulated for effecting the cleaning and/or polishing of teeth or to function as an antiseptic preparation for the oral cavity. Accordingly, the known dentifrices are limited in their applications and benefits, and for the most part are relatively ineffective for aiding, controlling and/or minimizing periodontal disease.

OBJECTS

It is therefore an object of this invention to provide a dentifrice which is formulated to synergistically effect the removal of dental plaque, reduce bacteria and to aid in the control of periodontal disease by its chemical and mechanical actions.

Another object is to provide a dentifrice which aids in the reduction of dental caries.

Another object is to provide a dentifrice which aids in combining chemically with the enamel structure of a tooth so as to render it more resistant to dental caries by enhancing the hardness of enamel so that the enamel is less likely to be demineralized by the acids formed by any adhering bacteria and their actions on sugar substances.

Another object is to provide a dentifrice formed as a stable paste to aid, eliminate or reduce periodontal disease and to prevent dental caries.

BRIEF SUMMARY OF THE INVENTION

The foregoing objects and other features and advantages are attained by a tooth and gum dentifrice which is formulated as a stable paste comprising of from 15% to 25% by weight of sodium bicarbonate, from 7.5% to 15% by weight of calcium carbonate, from 6% to 11% of carbamide peroxide in an anhydrous glycerine, from 0.5% to 1.5% of acidulated sodium fluoride of a low pH, e.g. from 1.8% by weight of sodium fluoride (NaF) and 0.20% phosphoric acid in $H_2O$, and the remainder, i.e. from 47.5% to 72% by weight of a paste which includes a synthetic detergent containing water, humectant, sorbitol, a thickening agent or binder, and a flavoring agent.

The dentifrice is preferably compounded by mixing the ingredients of the base paste with the appropriate portion of sodium bicarbonate. Subsequent to mixing of the sodium bicarbonate with the paste ingredients, the appropriate proportions of carbamide peroxide or urea peroxide $CH_4N_2O$. $H_2O_2$ and calcium carbonate are added. When the mixture is homogenized, the phosphoflourgel or sodium fluoride NaF is intermixed therewith. Upon completion of the mix, it is placed in light resistant and moisture proof containers or tubes.

FEATURES

A feature of this invention resides in the formulation of a tooth and gum dentifrice as a stable paste which will aid in controlling and/or reduction of periodontal disease as well as to aid in the reduction of dental caries.

Another feature resides in a dentifrice composition formulated to synergistically effect a chemical and mechanical action to remove dental plaque and reduce bacteria.

Other features and advantages will become readily apparent in view of the following description.

DETAILED DESCRIPTION

This invention is directed to a tooth and gum paste which is composed of a combination of various ingredients in a manner to formulate a stable paste which synergistically effects a chemical and mechanical action to affect the removal of dental plaque from the teeth and to reduce the bacterial level. The resultant effect is to aid the control and removal of incipient periodontal disease as well as to aid in the reduction of dental caries.

Essentially, the tooth and gum dentifrice comprises a formulation of sodium bicarbonate ($NaHCO_3$); calcium carbonate ($CaCO_3$); urea peroxide, i.e. in a paste carrier which includes a detergent, natural or synthetic, a humectant sorbitol, a thickening agent or binder, and a flavoring agent. The formulation, if desired, may also include a flouride as such flouride has been shown to be effective in aiding the enamel of teeth to become harder and more caries resistant.

Preferably, urea peroxide or carbamide peroxide in a water free gel base is used. In the formulation as herein set forth, the carbamide peroxide functions to adhere to the tissues and thereby it remains in place for a relatively long period of time while releasing more nacent oxygen to aid in debriding tissues and to inhibit odor forming bacteria. It also effects a foaming action which mechanically tends to raise the plaque and bacteria from incipient periodontal lesions and prevents them from releasing their destructive enzymes in the gum pocket. As the carbamide peroxide reaches the oral cavity, it disassociates into urea and peroxide. The hydrogen peroxide in the presence of peroxidase and catalase causes free oxygen ($O_2$) to be released. The free oxygen ($O_2$) has a bactericidal effect on the anaerobic bacteria to produce an anticaries and antiplaque effect.

In the bacterial plaque, the urea is turned into $NH_3$ and carbonic acid by the enzyme urease. This raises the acidified plaque to a more neutral ph and reduces the rate of tooth demineralization to render the tooth more resistant to caries by fermented carbohydrates. Thus, in the formulation, the carbamide peroxide has an anticaries and antiplaque effect on the teeth.

The calcium carbonate ($CaCO_3$) portion of the formulation is used as an abrasive and polishing agent. It too performs a mechanical action on the teeth to also aid in the removal of plaque and bacterial therefrom, as well as any food particles and stains from the tooth structure.

The sodium bicarbonate ($NaHCO_3$) portion of the formulation also has an abrasive action on the teeth to effect the removal of dental plaque, bacteria, food particles and stain from the tooth surfaces.

Also included in the formulation is a fluoride for combining chemically into the enamel structure of the teeth so as to cause the enamel to become harder, and thereby render the teeth to be less likely to demineralize by the acids formed by any adhering bacteria and their action on sugar substances.

EXAMPLE 1

The general formulation of the tooth and gum dentifrice is made as follows:

Sodium bicarbonate ranging from 15–25% by weight.
The sodium bicarbonate may include a #325 grit.
Calcium carbonate ranging from 7.5–15% by weight.
Carbamide peroxide in an anhydrous glycerin ranging from 6–11% by weight.
Acidulated sodium flouride of a low ph ranging from 0.5 to 1.5% by weight.
And the remainder of a paste i.e., ranging from 47.5 to 72% by weight.

The acidulated sodium flouride comprises a 1.8% NaF and 0.20% phosphoric acid in water (H₂O); i.e., phosphoflor gel.

The paste carrier comprises a mixture of a detergent, e.g. synthetic detergent containing water, a humectant, sorbital, and a thickening agent or binder. Also, the paste may be flavored by a suitable flavoring agent.

A preferred paste or carrier may include
18% by weight of sorbitol
1.5% by weight of sodium lauryl sulfate
9.9% by weight of glycerol
29% by weight of water
Remainder by weight comprising miscellaneous binder which may include flavor, sweeteners and a preservative.

The humectant sorbitol portion of the paste prevents loss of water when exposed to air. The thickening agent or binder prevents the separation of the liquid and solid ingredients. The thickening agent or binder comprised of gum tragacant and gum karaya (natural) seaweed colloid-sodium alginate and synthetic cellulose, i.e. Na carboxymethylcellulose or methylcellulose. A foaming agent such as sodium lauory sulfate and sodium N laurylsacrosinate. A sweetener such as saccharin and/or a suitable flavoring ingredient such as mint or the like may be included in the paste or carrier portion.

The above noted tooth and gum dentifrice is formulated by combining the paste comprising of the synthetic detergent, humectant sorbitol, thickening agent or binder and a flavoring agent with the sodium bicarbonate. When the paste and sodium bicarbonate has been thoroughly mixed, the carbamide peroxide and calcium carbonate are added in their respective proportions. When this mixture is homogenized, the phosphoflourgel is intermixed therewith.

Upon completion of the mix as herein set forth, it is placed in a light resistant and moisture proof container or tube.

The tooth and gum paste so formulated, is preferably used immediately after meals, or as soon thereafter as feasible. The formulated paste when used in conjunction with dental floss enables the preparation to be further dispensed into the incipient periodontal pockets to enhance the formulation in the reduction of food, plaque and bacterial action.

EXAMPLE 2

A specific tooth and gum formulation is made as follows:

| Sodium bicarbonate | 15% by weight |
| --- | --- |
| Calcium carbonate | 8% by weight |
| Carbamide peroxide | 8.5% by weight |
| Acidulate NaF of a low ph | .5% by weight |
| Paste carrier | 68% by weight | whereby the paste is formulated of the ingredients set forth in Example 1.

EXAMPLE 3

Another specific formulation of the tooth and gum dentifrice comprises:

| Sodium bicarbonate | 25% by weight |
| --- | --- |
| Calcium carbonate | 15% by weight |
| Carbamide peroxide | 10% by weight |
| Acidulated NaF | .75% by weight |
| Paste carrier | 49.25% by weight | wherein the paste is formulated of the ingredients defined in Example 1.

The combination of the foregoing noted ingredients form an effective and stable paste composition which gives it the ability to aid in the prevention of gum (periodontal) disease and aid in the reduction of dental caries, as well as to inhibit the more rapid spread of the decay process. The foregoing formulation further effects a stable composition to effect a synergism of actions in a singular preparation which can be readily applied to the teeth and gums by conventional brushing.

While the present invention has been described with respect to a particular embodiment, it will be understood that variations and modifications can be made without departing from the spirit or scope of the invention.

What is claimed is:

1. A tooth and gum dentifrice composition in the form of a stable paste, for controlling and minimizing incipient periodontal disease and for aiding in the reduction of dental plaque comprising from about 15% to 25% by weight of sodium bicarbonate, from about 7.5% to 15% by weight of calcium carbonate, from about 6% to 11% by weight of carbonide peroxide in anhydrous glycerin, from about 0.5% to 1.5% by weight of acidulated sodium flouride of a low ph, and from about 47.5% to 72% by weight of a paste including a synthetic detergent containing water, a humectant, sorbitol, a binder, and a flavoring agent.

2. A tooth and gum dentifrice composition in the form of a stable paste for aiding in the control and removal of periodontal lesions and for the removal of dental plaque and minimizing dental caries consisting essentially of
approximately 15% by weight of sodium bicarbonate,
approximately 8% by weight of calcium carbonate,
approximately 8.5% by weight of urea peroxide,
approximately 0.5% by weight of a sodium flouride of a low ph, and
the remainder of a paste of a mixture of synthetic detergent containing H₂O, a humectant, sorbitol and a thickening agent.

3. A tooth and gum dentrifice as defined in claim 2 wherein said remainder paste includes a flavoring agent.

4. A tooth and gum dentifrice composition in the form of a stable paste for aiding in the control and removal of periodontal lesions and for the removal of dental plaque and for minimizing dental carries consisting essentially of
approximately 25% by weight of sodium bicarbonate,
approximately 15% by weight of calcium carbonate,
approximately 10% by weight of urea peroxide,
approximately 0.75% by weight of sodium flouride of a low pH;
and approximately 49.25% by weight of a paste including a synthetic detergent containing H₂O, a humectant, sorbitol, a binder and a flavoring agent.

* * * * *